United States Patent [19]

Tabor et al.

[11] Patent Number: 4,547,368
[45] Date of Patent: Oct. 15, 1985

[54] HEPATITIS B CORE ANTIGEN VACCINE MADE BY RECOMBINANT DNA

[75] Inventors: Edward Tabor, Rockville; Robert J. Gerety, Potomac, both of Md.

[73] Assignee: The United States of America as represented by the Secretary of the Department of Health and Human Services, Washington, D.C.

[21] Appl. No.: 637,880

[22] Filed: Aug. 6, 1984

Related U.S. Application Data

[63] Continuation-in-part of Ser. No. 563,369, Dec. 20, 1983.

[51] Int. Cl.$^4$ .............................................. A61K 39/29
[52] U.S. Cl. .................................. 424/89; 435/172.3; 435/235
[58] Field of Search .............. 424/89; 435/172.3, 235

[56] References Cited

U.S. PATENT DOCUMENTS 4,100,267  7/1978  Shaw ........................................ 424/1
4,102,996  7/1978  McAleer et al. ...................... 424/89

OTHER PUBLICATIONS

Hoofnagle et al., The New Eng. J. of Med., 290:1336 (1974).
Hoofnagle et al., Lancet, 2:869 (1973).
Barker et al., J. of Virology, 14:1552 (1974).
Shaw et al., J. of Virology, 12:1598 (1973).
Tabor and Gerety, Lancet, 1:172 (letter), 1984.
Stahl et al. Proc. Natl. Acad. Sci., 79:1606–1610, 1982.
Tabor et al., Lancet, Jan. 21, 1984, p. 172.
Tabor et al., Transfusion, 21(3), May/Jun. 1981, pp. 366–371.
Tabor et al., J. Med. Virol., 6:91–99 (1980).
Neurath et al., J. Gen. Virol., 42:645–649 (1979).
Hoofnagle, N. Eng. J. Med., 298(25):1379–1383, Jun. 22, 1978.
Purcell et al., Am. J. Clin. Pathol, Jul. 1978, pp. 159–169.
Hansson, J. Clin. Microbiol., 6(3):209–211, Sep. 1977.
Tabor et al., J. Immunol., 117(5) (Part 2):2038–2040, Nov. 1976.
Hoofnagle, Am. J. Med. Sci., 270(1):179–187 (1975).
Hoofnagle, Develop. Biol. Stand., 30:175–185 (1975).
Krugman, Develop. Biol. Stand., 30:363–367 (1975).
Krugman, N. Engl. J. Med., 290:1331–1335, Jun. 13, 1974.
Barker et al., Adv. Int. Med., 23:327–351 (1976).

Primary Examiner—Shep K. Rose
Attorney, Agent, or Firm—John S. Roberts, Jr.

[57] ABSTRACT

Disclosed is a a vaccine effective for primates, such as chimpanzees, and against hepatitis B virus (HBV) using hepatitis B core antigen (HBcAg) made by recombinant DNA. Chimpanzees immunized with the vaccine were protected against hepatitis B.

3 Claims, No Drawings

HEPATITIS B CORE ANTIGEN VACCINE MADE BY RECOMBINANT DNA

This is a continuation-in-part application of pending Ser. No. 563,369 filed Dec. 20, 1983, in the names of Edward Tabor and Robert J. Gerety for "Hepatitis B Core Antigen Vaccine."

BACKGROUND OF THE INVENTION

The discovery of hepatitis B surface antigen (HBsAg, Australian antigen, or hepatitis-associated antigen) represented a major scientific breakthrough in the characterization and prevention of hepatitis B virus (HBV). The development of a vaccine to protect against HBV, using purified hepatitis B surface antigen (HBsAg) resulted in protection of up to 96% of those immunized. As of the present time, no good explanation has been found for the failure of the HBsAg vaccine to protect certain individuals. At least 5% of recipients of the currently available hepatitis B vaccine are not protected against subsequent HBV infection.

In the early 1970s a second antigen of HBV was discovered, the hepatitis B core antigen (HBcAg). This is located on the internal component of HBV as well as on 27 nm HBcAg particles found in the liver during chronic infection. An earlier application disclosed the preparation of a vaccine against HBV using HBcAg purified from infected liver cells.

The present invention discloses the preparation of a vaccine against HBV using HBcAg prepared using recombinant DNA technology. This vaccine has been tested in chimpanzees, protecting them against HBV infection.

UTILITY STATEMENT

The vaccine of this invention is useful either alone or in combination with vaccines made with HBsAg as a vaccine containing 50 μg of HBcAg and 20 ug of HBsAg. A preferred combination is one with a majority of HBcAg in weight percent. It is expected that these vaccines will provide both longer protection and more effective protection than the vaccines made solely from HBsAg. Of greatest importance, a combination vaccine is particularly needed for dialysis patients, a principle group of recipients of hepatitis B vaccines, since the existing vaccines are not fully effective in them. This vaccine also is needed for the 5% (or more) of recipients of the currently available HBV vaccine who do not respond to it.

Furthermore, greater safety will be achieved by use of the vaccine of this invention. Use of an HBcAg vaccine avoids the chance of inclusion of the unknown products of the virus genome which is located adjacent to the genome for HBsAg, and which has concerned many who have worked on developing recombinant HBsAg vaccines. Use of a recombinant HBcAg vaccine will reduce concerns which might arise from the use of HBcAg derived from infected liver, plasma, or serum since the gene product is an antigen without any nucleic acid which would have to be removed by purification techniques.

Use of a recombinant HBcAg vaccine permits the inexpensive production of larger quantities of vaccine than could be produced using HBcAg derived from liver, plasma, or serum. Its effective use in chimpanzees reiterates its usefulness in primates as a vaccine.

SUMMARY OF THE INVENTION

The present invention is a new vaccine against the hepatitis B virus prepared from HBcAg, a well-characterized antigen associated with the 27 nm core of the HBV. The preferred method of obtaining the HBcAg is by preparing clones of prokaryotic or eukaryotic cells by recombinant DNA techniques, which contain the gene for HBcAg integrated in the host cell genome.

The core antigen may be purified by any suitable means. The preferred method of the present invention is differential centrifugation. The purity of a core antigen preparation is confirmed by immune electron microscopy and radioimmunoassay.

MATERIAL INFORMATION DISCLOSURE

U.S. Pat. No. 4,100,267 (Shaw) and Shaw et al, *Journal of Virology*, Vol. 12, p. 1598 (1973), detail one method of producing hepatitis core antigen and antibody. The serum developed by Shaw, from A-2 plaque virus, is not a vaccine.

U.S. Pat. No. 4,102,996 (McAleer et al) discloses a method of preparing HBcAg from HBV ("Dane particles") from plasma and a method for increasing the HBcAb (antiHBc) titer in individuals already recovered from HBV infectious to produce an immune globulin. Therefore, this disclosure is not a vaccine.

Hoofnagle et al, *The New England Journal of Medicine*, Vol. 290, p. 1336 (1974); Hoofnagle et al, *Lancet*, Vol. 2, p. 869 (1973); and Barker et al, *J. of Virology*, Vol. 14, p. 1552 (1974) all disclose preliminary discoveries, experiments, and background dealing with HBcAg. The present vaccine was ultimately developed from these early discoveries.

Tabor and Gerety, "Possible Role of Immune Responses to Hepatitis B Core Antigen in Protection Against Hepatitis B Infections," *Lancet*, 1:172 (letter), 1984.

Stahl et al, "Hepatitis B Virus Core Antigen: Synthesis in *Excherichia coli* and Application in Diagnosis," *Proc. Natl. Acad. Sci.*, 79:1606–1610, 1982.

SPECIFIC DISCLOSURE

Cloned HBcAg was provided by Dr. K. Murray, Department of Molecular Biology, University of Edinburgh, Scotland. DNA from HBV was cloned into plasmid PBR322 and propagated in *E. coli* as a series of fragments produced by digestion with restriction endonucleases and as entire molecules after joining to plasmid or alpha phage vectors. Fragments of HBV DNA cloned into the Pst I restriction site in the beta lactamase gene carried by plasmid PBR322 directed the synthesis of HBcAg in *E. coli*. The HBcAg produced was readily detected by solid-phase radioimmunoassay and had the capacity to induce specific anti-HBc responses.

The HBcAg may be administered in combination with an adjuvant or in aqueous form. Suitable adjuvants include, but are not limited to, aluminum hydroxide and Freund's adjuvant. The HBcAg is administered as a vaccine by any of the following routes: subcutaneous or intramuscular.

EXAMPLES

The examples illustrate the protective ability of the vaccine in chimpanzees. For the purposes of this invention, a chimpanzee is considered a surrogate human, permitting controlled evaluation of the vaccine and the HBV used for challenge in a protected environment. Immune responses to HBV antigens have been shown to be identical in chimpanzees and humans.

EXAMPLE 1

A chimpanzee (No. 1200) was injected subcutaneously with the cloned HBcAg emulsified in complete Freund's adjuvant. A second and a third dose were administered 2 and 6 weeks later in incomplete Freund's adjuvant. The first dose consisted of 100 ug of HBcAg; the two later injections contained 50 ug of HBcAg. Following immunization, anti-HBc developed beginning one week after the first dose and reached a peak titer of 1:100 at week 8. Neither HBsAg or anti-HBs could be detected in any of the weekly serum samples.

Following challenge with 1,000 chimpanzee infectious doses of hepatitis B virus at week 10, no serologic evidence of hepatitis B virus infection could be detected during 24 weeks of follow-up.

EXAMPLE 2

A chimpanzee (No. 1000) was immunized with 20 μg of HBsAg and 50 μg of cloned HBcAg subcutaneously at zero, one, and six months. Anti-HBs and anti-HBc developed by two months. Testing of weekly serum samples revealed no detectable HBsAg. When challenged at 12 weeks with 1,000 chimpanzee infectious doses of hepatitis B virus, no evidence of hepatitis B developed during 12 months of evaluation.

We claim:

1. A method of protecting chimpanzees by administering a vaccine prepared by a process which comprises centrifuging and isolating HBcAg from the supernatant fluid of cloned cells containing recombinant hepatitis B virus DNA, mixing said HBcAg with a suitable adjuvant to form a vaccine, and injecting said vaccine into a chimpanzee.

2. A method of protecting chimpanzees from hepatitis B virus which comprises subcutaneously injecting said chimpanzees with a vaccine which is a mixture of (a) HBcAg prepared from cloned cells containing recombinant hepatitis B virus DNA and (b) HBsAg.

3. The method of claim 2 in which HBcAg is present in the amount of approximately 50 μg and the HBsAg is present in the amount of approximately 20 μg.

* * * * *